United States Patent [19]
Wessel et al.

[11] Patent Number: 5,886,218
[45] Date of Patent: Mar. 23, 1999

[54] PROCESS FOR PREPARING 4, 5-DICHLORO-2-METHYLBENZOIC ACID

[75] Inventors: Thomas Wessel, Frankfurt; Peter Koch, Obertshausen, both of Germany

[73] Assignee: Hoechst Aktiengesellschaft, Frankfurt, Germany

[21] Appl. No.: 846,313

[22] Filed: Apr. 30, 1997

[30] Foreign Application Priority Data

May 2, 1996 [DE] Germany ............. 196 17 558.5

[51] Int. Cl.$^6$ ............................................. C07C 51/16
[52] U.S. Cl. .......................................... 562/419; 562/493
[58] Field of Search ............................................. 562/419

[56] References Cited

U.S. PATENT DOCUMENTS

| | | | |
|---|---|---|---|
| 1,930,449 | 10/1933 | Brunson | 562/419 |
| 3,236,623 | 2/1966 | Klein . | |
| 4,393,232 | 7/1983 | Maurer | 562/419 |
| 5,093,529 | 3/1992 | Schmand | 568/323 |
| 5,296,636 | 3/1994 | Siegel | 562/419 |
| 5,607,898 | 3/1997 | Nakamura | 504/282 |

FOREIGN PATENT DOCUMENTS

| | | |
|---|---|---|
| 1255330 | 6/1989 | Canada . |
| 0 176 026 | 4/1986 | European Pat. Off. . |
| 1 330 953 | 12/1963 | France . |
| 3840371 | 5/1990 | Germany ............. 562/419 |

OTHER PUBLICATIONS

Lutz, et al, J. Organic. Chemistry 12:617 (1947).
Textbook of Organic Chemistry, Carl R. Noller, Second Edition, (1958) p. 166.

*Primary Examiner*—Michael L. Shippen
*Attorney, Agent, or Firm*—Scott E. Hanf

[57] ABSTRACT

The present invention relates to a process for preparing 4,5-dichloro-2-methylbenzoic acid and also its salts in high yields and in high purities by reacting 3,4-dichlorotoluene with acetyl chloride or chloroacetyl chloride in the presence of a Friedel-Crafts catalyst and subsequently oxidizing the acetylated intermediate to give the carboxylic acid.

14 Claims, No Drawings

PROCESS FOR PREPARING 4,5-DICHLORO-2-METHYLBENZOIC ACID

The present invention relates to a process for preparing 4,5-dichloro-2-methylbenzoic acid and also its salts in high yields and in high purities by reacting 3,4-dichlorotoluene with acetyl chloride or chloroacetyl chloride in the presence of a Friedel-Crafts catalyst and subsequently oxidizing the acetylated intermediate to give the carboxylic acid.

4,5-Dichloro-2-methylbenzoic acid and the acetylated precursors are, like many ortho-substituted aromatic carboxylic acid derivatives important intermediates for the preparation of pharmaceuticals and crop protection agents.

It is known that 4,5-dichloro-2-methylacetophenone can be prepared by reacting 2 mol of 3,4-dichlorotoluene with 2 mol of acetyl chloride and aluminum chloride at 100° C. (Lutz et al., J. Org. Chem. 1947, 12, 617–686 or DE-A 2142564). According to this process, however, the acetyl compound is obtained as the approximately pure isomer in 60% yield after being recrystallized twice from ethanol. Chloroacetylations of 3,4-dichlorotoluene have not hitherto been studied. In U.S. Pat. No. 3,236,623, 4,5-dichloro-2-methylbenzoic acid is obtained in a mixture with 3,4-dichloro-2-methylbenzoic acid by chlorination of dichloroorthoxylane, subsequent reaction with sodium formate to give methyldichlorobenzyl formate and nitric acid oxidation, with the purification being carried out by means of fractional crystallization from benzene.

In view of this prior art, it is an object of the present invention to provide a process for preparing 4,5-dichloro-2-methylbenzoic acid which is improved in terms of ecological and occupational hygiene aspects, reduces the pollution of wastewater and avoids the use of toxicologically questionable solvents while giving high-purity products in high yield in a technically simple manner.

The present invention provides a process for preparing 4,5-dichloro-2-methylbenzoic acid or its salts of the formula I,

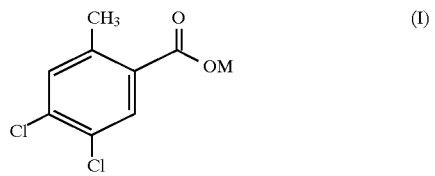

where M is hydrogen or an equivalent of an alkali or alkaline earth metal, which comprises acetylating or haloacetylating 3,4-dichlorotoluene in the presence of a Friedel-Crafts catalyst, oxidizing the isomer mixture obtained in a haloform reaction in the presence of an alkali metal hydroxide or alkaline earth metal hydroxide, subsequently purifying the 4,5-dichloro-2-methylbenzoic acid in the form of its alkali metal or alkaline earth metal salt and, if desired, converting the salt into the free acid.

As acetylating, agents, preference is given to using acetyl chloride, chloroacetyl chloride or acetic anhydride.

Suitable Friedel-Crafts catalysts are, in particular aluminum chloride, zinc chloride and iron(III) chloride, with aluminum chloride being particularly preferred.

According to the process of the invention, the Friedel-Crafts catalyst is usually initially charged in excess 3,4-dichlorotoluene and the acetylating agent is metered in. However, it is also possible to meter the Friedel-Crafts catalyst into the initially charged acetylating agent in 3,4-dichlorotoluene.

After the reaction is complete and the reaction mixture has been hydrolyzed and the phases have been separated, excess 3,4-dichlorotoluene is recovered by distillation and can again be added to a subsequent batch. Vacuum distillation or steam distillation without prior separation of the phases are here the preferred embodiments.

The acetylated or chloroacetylated intermediate can also be obtained by distillation under reduced pressure. A further preferred possibility for isolating the product, particularly in the case of chloroacetylations, is filtration after 3,4-dichlorotoluene has previously been removed by steam distillation and the product has been granulated by cooling while stirring.

The reaction of 3,4-dichlorotoluene with acetyl chloride, chloroacetyl chloride or acetic anhydride is preferably carried out at temperatures of from 10° to 90° C., particularly preferably from 20° to 70° C. and very particularly preferably from 30° to 50° C.

The subsequent haloform oxidation is preferably carried out directly on the isomer mixture resulting from the Friedel-Crafts acetylation. Suitable alkali metal hydroxides and alkaline earth metal hydroxides are, for example, lithium, sodium, potassium, rubidium, cesium, magnesium, calcium, strontium and barium hydroxide. Preferred alkali metal hydroxides are sodium and potassium hydroxide, very particularly preferably sodium hydroxide.

Oxidizing agents employed are hypohalites or halogens in alkaline solution, e.g. hypochlorite, hypobromite or hypoiodite, with hypochlorite and hypobromite being preferred. Very particular preference is given to hypochlorite in the form of the commercially available chlorine bleaching liquor, with in turn very particular preference being given to concentrations having from about 50 g to 200 g of active chlorine per liter of solution.

The order in which the reactants are combined in the oxidation can be varied. For example, acetylated or chloroacetylated intermediate can be metered into the oxidizing agent. However, preference is given to metering oxidizing agent into the initially charged acetophenone. If chlorine bleaching liquor is used as oxidizing agent in the haloform reaction, from 1.5 to 4 times the molar amount of active chlorine, based on the acetyl or chloroacetyl compound, can be advantageous.

The acetylated intermediates are preferably oxidized using from 2.8 to 3.5 times the molar amount of active chlorine, while chloroacetylated intermediates are preferably reacted with from 1.7 to 2.4 times the amount of active chlorine.

Depending on the type of procedure, the oxidation stage of the process of the invention can be carried out cold or hot. The reaction is preferably carried out between 0° C. and 100° C. Particular preference is given to temperatures between 20° C. and 90° C. and very particular preference is given to temperatures between 70° C. and 90° C.

The product is isolated by customary work-up methods via the alkali metal or alkaline earth metal 4,5-dichloro-2-methylbenzoate. For the subsequent purification step for the salt obtained, preference is given to setting a pH range which allows isomeric dichloromethylbenzoic acids to be separated off. Such a purification is preferably carried out at a pH between 8 and 12, very particularly preferably between 9 and 10. Particularly good results are achieved by skillful exploitation of the solubility properties of the salts. The isolation of a crystalline 4,5-dichloro-2-methylbenzoate is a preferred purification method. If the salt is only sparingly soluble in the medium when cold, substantial precipitation can be achieved by cooling a previously hot solution or suspension, e.g. to room temperature or even below. In the case of a greater solubility, it is possible, for example, to distill off part of the water or substantial precipitation can be achieved by addition of other salts (salting out) or of organic precipitates. The material which has crystallized out is then separated off in a customary way, e.g. by filtration or centrifugation. If desired, the product can be washed in addition.

The 4,5-dichloro-2-methylbenzoate which has thus been isolated in some form can, if the free acid is to be prepared, be converted into the acid by methods known per se, for example by introduction into aqueous inorganic acids, preferably hydrochloric or sulfuric acid. The precipitated acid can then be separated off in a customary way, e.g. by filtration or centrifugation, washed and dried.

The alkali metal and alkaline earth metal salts of 4,5-dichloro-2-methylbenzoic acid prepared by the process of the invention and also the free acid obtained therefrom have high purities of >98% and are thus particularly suitable as intermediates in the synthesis of pharmaceuticals and crop protection agents.

Sodium 4,5-dichloro-2-methylbenzoate and 2-chloro-1-(4,5-dichloro-2-methylphenyl)ethanone are not previously known and are thus likewise subject matter of the present invention.

EXAMPLE 1 a) Friedel-Crafts acetylation of 3,4-dichlorotoluene using acetyl chloride 450 g of 3,4-dichlorotoluene (about 97% pure according to GC, corresponding to 2.7 mol) are placed in a multineck flask fitted with precision glass stirrer, dropping funnel, internal thermometer and reflux condenser. While stirring, 161.5 g of anhydrous aluminum chloride (1.21 mol) are added to this solution a little at a time over a period of about 15 minutes. The mixture is subsequently heated to an internal temperature of 42°–43° C. and 90 g of acetyl chloride (1.15 mol) are then metered in over a period of about 45–60 minutes in such a way that the internal temperature does not exceed 50° C. After the acetyl chloride has been run in, the mixture is stirred further for about 4 h at 50° C.

Hydrolysis 500 g of ice, 250 ml of water and 71 g of concentrated 36% strength hydrochloric acid are placed in a multineck flask fitted with precision glass stirrer and internal thermometer and stirred. The acetylation mixture, which has been cooled to room temperature, is carefully added to this ice solution. It is rinsed in with a further 125 g of 3,4-dichlorotoluene and the hydrolysis mixture is stirred further for 30 minutes.

The organic phase is then separated off. Subsequently, the starting material 3,4-dichlorotoluene is distilled off under reduced pressure at 20 mbar and a top temperature of 83° C. via a distillation attachment with packed column (20 cm height, packing: 6 mm Raschig rings). The product is distilled under reduced pressure at 20 mbar and a top temperature of 125° C.

387 g of 3,4-dichlorotoluene (97% pure according to GC, corresponding to 2.4 mol, corresponding to 67% of the total amount used) are obtained and this is added directly to a subsequent batch.

Also obtained are 210 g of (4,5-dichloro-2-methylphenyl)ethanone in the form of an isomer mixture having an isomer ratio of about 92:8 (according to GC) based on the desired isomer (corresponding to 1.04 mol as obtained, corresponding to 30 mol % based on the dichlorotoluene used). This corresponds to a total yield of 97% of theory.

Melting point: 49° C. (isomer mixture), after recrystallizing twice, the melting point reaches 55°–57° C. for isomerically pure product (ethanol)

$^1$H-NMR (300 MHz, [D$_6$]DMSO): 2.4 ppm (CH$_3$C=, 3H), 2.6 (CH$_3$C=, 3H), 7.6 (H ar., 1H), 8.0 (H ar., 1H).

$^{13}$C-NMR (75.5 MHz, [D$_6$]DMSO): 19.9 ppm (CH$_3$), 29.7 (CH$_3$), 128.3 (—C=), 131.0 (HC=), 133.2 (HC=), 133.7 (—C=), 137.6 (—C=), 138.1 (—C=), 199.7 (—C=O).

GC-MS (m/e): 202, 204 (27%, 20%) [M$^+$], 187, 189, 191 (100%, 68%, 6%) [M$^+$—CH$_3$].

b) Oxidation of (4,5-dichloro-2-methylphenyl)ethanone 203 g of (4,5-dichloro-2-methylphenyl)ethanone (1 mol as obtained, isomer mixture from the process as described under a)) are placed in a 4l multineck flask fitted with feed pump for chlorine bleaching liquor, precision glass stirrer, thermometer, measuring point for R$_H$- measurement and pH electrode. 400 ml of water are added and the mixture is heated to 90° C. The pH is adjusted to 9–10 using a little 50 strength sodium hydroxide solution. 1520 ml of chlorine bleaching liquor (145 g of active chlorine/l determined by titration, corresponding to 3.1 mol) are then metered in at this temperature over a period of about 3–4 hours. At the end, the excess of NaOCl is destroyed using a little sodium pyrosulfite and the mixture is cooled to 10° C., with the sodium salt precipitating as fine crystals. The precipitated salt is filtered off and washed with 240 g of saturated sodium chloride solution (aqueous). This gives about 270 g of moist sodium salt which can be dried for analytical purposes.

Melting point: 237°–240° C.

HPLC: 98.0% pure $^1$H-NMR (300 MHz, [D$_6$]DMSO): 2.4 ppm (CH$_3$, 3H), 7.4 (H ar., 1H), 7.8 (H ar., 1H).

$^{13}$C-NMR (75.5 MHz, [D$_6$]DMSO): 20.1 ppm (CH$_3$), 126.9 (—C=), 129.0 (—C=), 130.5 (HC=), 131.6 (HC=), 137.2 (—C=), 141.7 (—C=), 170.0 (—C=O).

IR (KBr): 3392 cm$^{-1}$ (OH/H$_2$O, ss), 1700 (COOH, m), 1596 (C=C, s), 1568 (COO$^-$, ss), 1396 (COO$^-$, ss).

Stirring about 270 g of the sodium salt of 4,5-dichloro-2-methylbenzoic acid into 500 ml of water and 80 g of concentrated 36% strength hydrochloric acid, filtering off, washing with 250 ml of water and drying in vacuo gives the free acid.

178 g of 4,5-dichloro-2-methylbenzoic acid are obtained in the form of a white powder.

This corresponds to a yield of 94.2% of theory, based on the desired isomer.

Melting point: 177°–179° C.

HPLC: 98.4% pure $^1$H-NMR (300 MHz, [D$_6$]DMSO): 2.5 ppm (CH$_3$, 3H), 7.6 (H ar., 1H), 8.0 (H ar., 1H), COOH obscured.

EXAMPLE 2 a) Chloroacetylation of 3,4-dichlorotoluene 645 g of 3,4-dichlorotoluene (about 97% pure according to GC, corresponding to 4.0 mol) are placed in a multineck flask fitted with precision glass stirrer, dropping funnel, internal thermometer and reflux condenser. While stirring, 161.5 g of aluminum chloride (1.21 mol) are added to the starting material over a period of about 15 minutes. 124.3 g of chloroacetyl chloride (98% pure, corresponding to 1.08 mol) are subsequently metered into the suspension at 22°–25° C. in such a way that the temperature does not exceed 30° C. After the chloroacetyl chloride has been run in, the mixture is stirred further for 4 hours at 40° C.

Hydrolysis 600 g of ice and 60 ml of concentrated 36% strength hydrochloric acid are placed in a multineck flask fitted with stirrer and thermometer and the above mixture is carefully added. The mixture is rinsed in with a further 100 ml of 1N hydrochloric acid. 3,4-Dichlorotoluene is then continuously removed via a water separator, with the top temperature being 106°–108° C. After the removal of dichlorotoluene is complete, the mixture is cooled while stirring to 15° C., the product thus granulated is filtered off with suction, washed with 500 ml of water and dried in vacuo at 45° C. 460 g of steam-distilled 3,4-dichlorotoluene are recovered (93% pure according to GC, corresponding to 2.74 mol, corresponding to 70% of the total amount used, and containing 4 GC-% of product, corresponding to 2 mol % of the total amount used) and this can be added directly to a subsequent batch.

Also obtained are 235 g of 2-Chloro-1-(4,5-dichloro-2-methylphenyl)-ethanone in the form of an isomer mixture having an isomer ratio of 93.5:6.5 (according to GC) based on the desired isomer (corresponding to 1.01 mol as obtained, corresponding to 24 mol % based on the dichlorotoluene used). This corresponds to a total yield of 96% of theory.

Melting point: 75°–77° C. (isomer mixture)

$^1$H-NMR (300 MHz, [D$_6$]DMSO]: 2.2 ppm (CH$_3$C=, 0.1H), 2.4 (CH$_3$C=, 3.1H), 4.5 (CH$_2$, 0.2H), 5.2 (CH$_2$Cl, 1.9H), 7.6 (H ar., 0.1H), 7.6 (H ar., 0.9H), 8.0 (H ar., 0.1H), 8.2 (H ar., 0.9H).

$^{13}$C-NMR (75.5 MHz, [D$_6$]DMSO]: 19.5 ppm (CH$_3$), 49.1 (CH$_2$), 128.4 (—C=), 130.5 (HC=), 133.3 (HC=), 134.4 (—C=), 135.1 (—C=), 138.8 (—C=), 193.3 (C=O).

IR (KBR): 2991, 2956, 2934 cm$^{-1}$ (arom., aliph. CH, s), 1703 (C=O, ss), 1540 (C=C, ss), 1215 (CO—CH$_2$, ss).

GC-MS (m/e): 236, 238, 240 (9%, 7%, 2%) [M$^+$], 187, 189, 191 (100%, 62%, 14%) [M$^+$—CH$_2$Cl], 159, 161, 163 (42%, 24%, 6%) [M$^+$—CH$_2$Cl—CO].

b) Oxidation of 2-chloro-1-(4,5-dichloro-2-methylphenyl) ethanone

Using the procedure of Example 1b), 237 g (1 mol as obtained) of an isomer mixture as described in a) above in 200 ml of water are oxidized at 70° C. using 1050 ml of chlorine bleaching liquor (145 g of active chloride/l). The product is isolated via the sodium salt. The acid is then obtained in free form by stirring the salt into hydrochloric acid. After drying, this gives 138.2 g of 4,5-dichloro-2-methylbenzoic acid having a high isomer purity, corresponding to 75.2% of theory.

Melting point: 176°–178° C.

We claim:

1. A process for preparing 4,5-dichloro-2-methylbenzoic acid or its salts of the formula I,

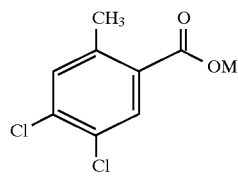

where M is hydrogen or one equivalent per mole of formula I of an alkali or alkaline earth metal, which comprises; acetylating or haloacetylating 3,4-dichlorotoluene with an acetylating agent in the presence of a Friedel-Crafts catalyst to obtain an isomer mixture, oxidizing said isomer mixture with an oxidizing agent in a haloform reaction in the presence of an alkali metal hydroxide or alkaline earth metal hydroxide, subsequently isolating the resulting alkali metal or alkaline earth metal salt of 4,5-dichloro-2-methylbenzoic acid and, optionally, converting the salt into the free acid.

2. The process as claimed in claim 1, wherein the acetylating or haloacetylating step is carried out in excess 3,4-dichlorotoluene.

3. The process as claimed in claim 1, wherein the acetylating agent is acetyl chloride, chloroacetyl chloride or acetic anhydride.

4. The process as claimed in claim 1, wherein the Friedel-Crafts catalyst comprises aluminum chloride.

5. The process as claimed in claim 1, wherein the acetylating step is carried out at a temperature in the range of from 10° to 90° C.

6. The process as claimed in claim 1, wherein the alkali metal hydroxide or alkaline earth metal hydroxide is lithium, sodium, potassium, rubidium, cesium, magnesium, calcium, strontium or barium hydroxide.

7. The process as claimed in claim 1, wherein said oxidizing agent is hypochlorite, hypobromite or hypoiodite.

8. The process as claimed in claim 1, wherein said resulting alkali metal or alkaline earth metal salt of 4,5-dichloro-2-methylbenzoic acid is isolated by crystallization at a pH between 8 and 12.

9. A process for preparing a 4,5-dichloro-2-methylbenzoate, comprising:

acetylating or haloacetylating 3,4-dichlorotoluene with an acetylating agent in the presence of a Friedel-Crafts catalyst to obtain an isomer mixture comprising the (4,5-dichloro-2-methylphenyl)ethanone or haloethanone intermediate, oxidizing said isomer mixture with an oxidizing agent selected from hypohalites or halogens in alkaline solution, in the presence of an alkali metal hydroxide or alkaline earth metal hydroxide to obtain the alkali metal or alkaline earth metal salt of 4,5-dichloro-2-methylbenzoic acid, and isolating said alkali metal or alkaline earth metal salt of 4,5-dichloro-2-methylbenzoic acid.

10. A process for the preparation of 4,5-dichloro-2-methylbenzoic acid which comprises carrying out the process of claim 9 and then converting said alkali metal or alkaline earth metal salt of 4,5-dichloro-2-methylbenzoic acid to the free acid.

11. The process as claimed in claim 9, wherein said acetylating agent is acetyl chloride, chloroacetyl chloride or acetic anhydride.

12. The process as claimed in claim 9, wherein said alkali metal or alkaline earth metal salt of 4,5-dichloro-2-methylbenzoic acid is isolated by crystallization at a pH between 8 and 12.

13. The process as claimed in claim 9, wherein said oxidizing agent is a hypochlorite, hypobromite or hypoiodite.

14. The process as claimed in claim 9, wherein said acetylating agent is chloroacetyl chloride, and the isomer mixture comprises 2-chloro-1-(4,5-dichloro-2-methylphenyl)ethanone.

* * * * *